US011466322B2

(12) United States Patent
Jo et al.

(10) Patent No.: US 11,466,322 B2
(45) Date of Patent: Oct. 11, 2022

(54) FLOURESCENT PROTEIN COMPOSITION FOR DNA SEQUENCE ANALYSIS AND METHOD FOR DNA SEQUENCE ANALYSIS USING SAME

(71) Applicant: SOGANG UNIVERSITY RESEARCH FOUNDATION, Seoul (KR)

(72) Inventors: Kyubong Jo, Seoul (KR); Seonghyun Lee, Seoul (KR); Jihyun Park, Gyeonggi-Do (KR); Eunji Shin, Seoul (KR)

(73) Assignee: SOGANG UNIVERSITY RESEARCH FOUNDATION, Seoul (KR)

( * ) Notice: Subject to any disclaimer, the term of this patent is extended or adjusted under 35 U.S.C. 154(b) by 204 days.

(21) Appl. No.: 16/427,438

(22) Filed: May 31, 2019

(65) Prior Publication Data
US 2020/0190580 A1 Jun. 18, 2020

(30) Foreign Application Priority Data

Dec. 13, 2018 (KR) .................. 10-2018-0161115

(51) Int. Cl.
*C12Q 1/6876* (2018.01)
(52) U.S. Cl.
CPC .................. *C12Q 1/6876* (2013.01)
(58) Field of Classification Search
None
See application file for complete search history.

(56) References Cited

U.S. PATENT DOCUMENTS

2010/0055701 A1 3/2010 Tong et al.
2012/0164754 A1* 6/2012 Rhee .................. C12Q 1/6813
977/774

FOREIGN PATENT DOCUMENTS

KR 10-2012-0071191 A 7/2012
KR 10-2016-0115553 A 10/2016
KR 10-2018-0097956 A 9/2018

OTHER PUBLICATIONS

Park (Analyst 2019 144 921-927 published Oct. 8, 2018).*
Lee (RSC Adv 2016, 6, 46291-46298).*
Van Mameren (PNAS Oct. 27, 2009 vol. 106 No. 43 pp. 18231-18236).*
Park, et al. (2019) "Single-molecule DNA visualization using AT-specific red and non-specific green DNA-binding fluorescent proteins\.", *Analyst*, 144(3):921-927.
Korean Office Action dated Jan. 17, 2020 issued in KR Patent Application No. 10-2018-0161115.
Written Decision on Registration from corresponding Korean Patent Application No. 10-2018-0161115, dated Jul. 29, 2020.

* cited by examiner

*Primary Examiner* — Amanda Haney
(74) *Attorney, Agent, or Firm* — Harness, Dickey & Pierce, P.L.C.

(57) ABSTRACT

The present invention relates to a composition for DNA sequence analysis and a method for DNA sequence analysis, the method comprising treating a sample with the composition. The composition of the present invention can attain efficient optical identification at a single-DNA molecule level by linking both an A/T-specific DNA-binder agent and an A/T-non-specific complementary DNA-binder agent to DNA, and thus can be helpfully used in studying chromosomal organization of genomes, protein immunolocalization, and the like.

7 Claims, 5 Drawing Sheets

Specification includes a Sequence Listing.

FLUORESCENT PROTEIN COMPOSITION FOR DNA SEQUENCE ANALYSIS AND METHOD FOR DNA SEQUENCE ANALYSIS USING SAME

CROSS-REFERENCE TO RELATED APPLICATION

This application claims priority to Korean Patent Application No. 10-2018-0161115, filed on Dec. 13, 2018, the entire contents of which are incorporated herein by reference.

FIELD

The present disclosure relates to a composition for DNA sequence analysis and a method for DNA sequence analysis using the same and, specifically, to a composition containing a DNA-binding fluorescent protein and a method for DNA sequence analysis, the method comprising treating a sample with the same.

BACKGROUND

Direct visualization of individual DNA molecules is very important because it allows for understanding biochemical events within the context of DNA sequences. Although sequencing technology at the single nucleotide level has advanced, biological problems still remain unsolved, which are limited by short read length and information loss within a large genome.

The ultimate goal of DNA analysis would be to acquire nucleotide sequences and epigenetic information directly from chromosomal DNA without fragmentation or amplification. Given these concerns, single DNA molecules are a promising platform to overcome limitations of current sequencing technology.

In this regard, optical mapping, which is a technique for gaining genetic information by visualizing a large DNA molecule, has been continually developed. This technique is a method to make barcode-like patterns from a single DNA molecule for visualization.

Meanwhile, conventional analysis methods using sequence-specific restriction enzymes retain the fundamental problem of DNA cleavage. Analysis methods using sequence-specific substances for A/T base pairs (Netropsin, etc.) and fluorescent dye markers raises the problem that YOYO-1, used as the fluorescent dye, causes light-induced DNA cleavage.

There is therefore a need for the development of a substance that can bind in a sequence-specific manner and fluoresce alone without causing DNA cleavage.

SUMMARY

Technical Problem

The present inventors endeavored to develop a substances capable of obtaining images of genome-specific molecules at a single-DNA molecule level. As a result, the present inventors confirmed that the use of both an NT-specific DNA binding protein and an A/T-non-specific complementary DNA binding protein can create a sequence-specific DNA map for efficient optical identification of a single DNA molecule even without separate sequencing, and then completed the present invention.

Therefore, a purpose of the present disclosure is to provide a composition for DNA sequence analysis.

Another purpose of the present disclosure is to provide a method for DNA sequence analysis.

Technical Solution

The present inventors endeavored to develop a substances capable of obtaining images of genome-specific molecules at a single-DNA molecule level. As a result, the present inventors confirmed that the use of both an NT-specific DNA binding protein and an A/T-non-specific complementary DNA binding protein can create a sequence-specific DNA map for efficient optical identification of a single DNA molecule even without separate sequencing.

The present invention is directed to a composition for DNA sequence analysis and a method for DNA sequence analysis using the same.

Hereinafter, the present invention will be described in detail.

In accordance with an aspect of the present invention, there is provided a composition for DNA sequence analysis, the composition containing: an adenine/thymine (A/T)-specific DNA binding protein linked with a first fluorescent protein; and an NT-non-specific DNA binding protein linked with a second fluorescent protein.

The first fluorescent protein and the second fluorescent protein may exhibit different colors differentiated from each other.

Specifically, the first fluorescent protein may exhibit red and the second fluorescent protein may exhibit green; the first fluorescent protein green and the second fluorescent blue; or the first fluorescent protein yellow and the second fluorescent protein sky blue.

The first fluorescent protein may be mCherry, DsRed2, mScarlet, mStrawberry, tdTomato, TagRFP, TagRFP-T, mApple, mRuby, mPlum, mKate2, mNeptune, or TagRFP657, but is not limited thereto.

The second fluorescent protein may be enhanced green fluorescent protein (eGFP), Emerald, Superfolder GFP, TagGFP2, mClover2, mClover3, mEos2, or mEos3.2, but is not limited thereto.

The adenine/thymine (A/T)-specific DNA binding protein may bind to DNA specifically to A/T nucleotide pair (W).

The A/T-specific DNA binding protein is a histone-like nucleoid-structuring (H-NS) protein or a high mobility group (HMG), but is not limited thereto.

The amino acid sequence of the histone-like nucleoid-structuring protein is represented by SEQ ID NO: 17.

The amino acid sequence of the high mobility group is represented by SEQ ID NO: 18.

The NT-non-specific DNA binding protein may bind to DNA non-specifically to NT nucleotide pair (W).

The NT-non-specific DNA binding protein is, but not limited to, a breast cancer 1 (BRCA1) protein or a protein having a structure of chemical formula 1 below:

$$(XY)_n, \quad \text{[Chemical Formula 1]}$$

wherein X and Y each may be independently any amino acid independently selected from lysine (K), tryptophane (W), or derivatives thereof; and wherein n may be an integer of 1 to 5.

The amino acid sequence of the BRCA1 protein is represented by SEQ ID O: 19.

The fluorescent protein (first or second fluorescent protein) and the DNA binding protein (NT-specific or NT-non-specific DNA binding protein) may be linked with to each other via a linker. Various kinds of linkers that can link a DNA binding protein and a fluorescent protein may be used according to the kind of fluorescent protein.

The linker may be a peptide linker comprising at least two amino acids selected from the group consisting of glycine (G), serine (S), lysine (K), and alanine (A).

The linker sequence may be, for example, GGSGG, but is not limited thereto.

The first fluorescent protein (or the second fluorescent protein) may be located at the N-terminal or C-terminal of the A/T-specific DNA binding protein (or NT-non-specific DNA binding protein), or may be located at both the N-terminal and C-terminal thereof.

The NT-specific DNA binding protein linked with the first fluorescent protein and the NT-non-specific DNA binding protein linked with the second fluorescent protein may be contained at a concentration ratio of 1:1-20, 1:1-10, 1:2-10, 1:3-10, 1:4-10, 1:5-10, 1:1-9, 1:1-8, 1:1-7, 1:1-6, 1:1-5, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or 1:20.

The DNA may be for example, a single DNA molecule, oligo DNA, a chromosome, a polytenechromosome, and a chromatin fiber, but is not limited thereto.

In the composition, the A/T-specific DNA binding protein linked with the first fluorescent protein preferentially binds to an NT-rich region of DNA, so that efficient optical identification of a single DNA molecule can be attained by linking both an NT-specific DNA binder agent and a A/T-non-specific complementary DNA binder agent to DNA.

Furthermore, the composition can analyze chemically modified or damaged DNA backbone, unlike conventional sequencing, and thus can be helpfully used at a single-DNA molecule level.

In accordance with another aspect of the present invention, there is provided a method for DNA sequence analysis, the method including treating a sample with a composition for DNA sequence analysis, the composition containing: an adenine/thymine (A/T)-specific DNA binding protein linked with a first fluorescent protein; and an NT-non-specific DNA binding protein linked with a second fluorescent protein.

The method may further include comparing the adenine/thymine (A/T) frequency of the entire genome of an analysis target and the NT frequency of the sample treated with the composition.

The sample may be, for example, a single DNA molecule, oligo DNA, a chromosome, a polytenechromosome, and a chromatin fiber, but is not limited thereto.

In the method, the DNA sequence of the analysis target can be analyzed by scanning the entire genomic NT frequency of the analysis target in silico map using a Python program and searching the most suitable alignment position between an image of the sample treated with the composition for DNA sequence analysis and the scanned entire genome NT frequency.

The overlapping description of the composition is omitted considering the complexity of the present specification.

Advantageous Effects

The present invention is directed to a composition for DNA sequence analysis and a method for DNA sequence analysis, the method comprising treating a sample with the composition. The composition of the present invention can attain efficient optical identification at a single-DNA molecule level by linking both an NT-specific DNA-binder agent and an NT-non-specific complementary DNA-binder agent to DNA, and thus can be helpfully used in studying chromosomal organization of genomes, protein immunolocalization, and the like.

Especially when the composition is a fluorescent protein having DNA binding ability, the composition facilitates production and induces mutations after the construction of genes, and thus has an advantage that various new properties can be imparted.

i) H-NS-mCherry and BRCA1-eGFP, ii) H-NS-mCherry and 2(KW)$_2$-eGFP, iii) 2HMG-mCherry and BRCA1-eGFP, iv) 2HMG-mCherry and 2(KW)$_2$-eGFP, v) H-NS-mCherry and 2HMG-eGFP, and vi) 2(KW)$_2$-mCherry and BRCA1-eGFP.

Figure 3A:
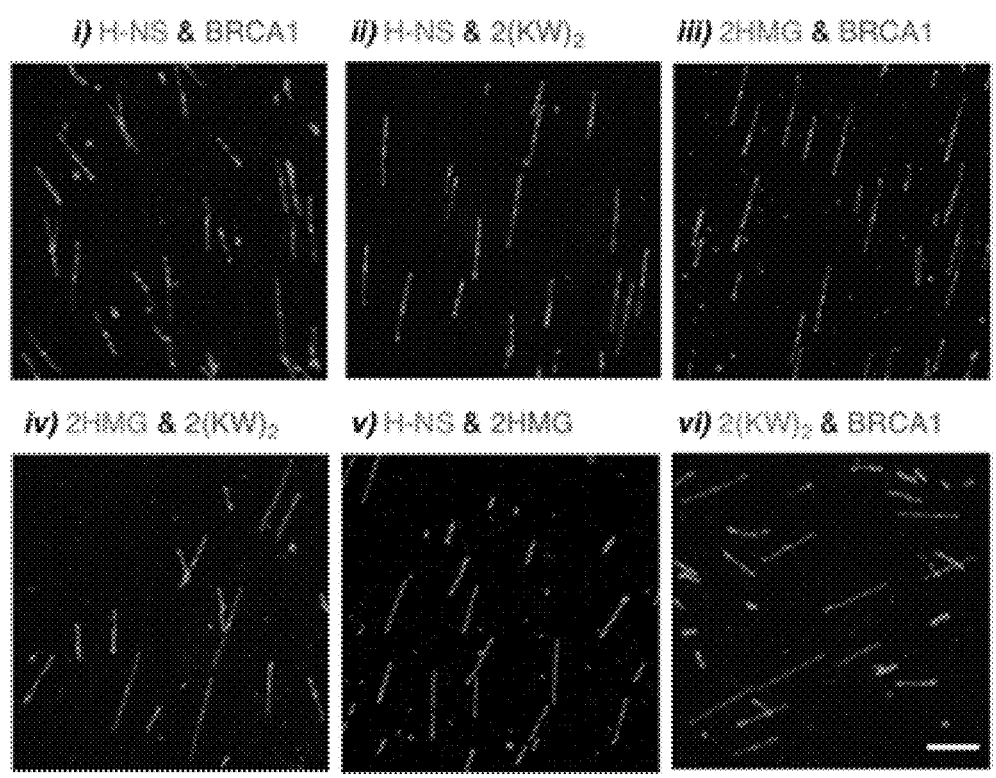
FIG. 3A shows λ DNA molecules stained with various combinations of fluorescent protein-DNA binding protein according to an embodiment of the present invention. The respective combinations are shown below (scale bar: 10 μm)
Figure 3B:
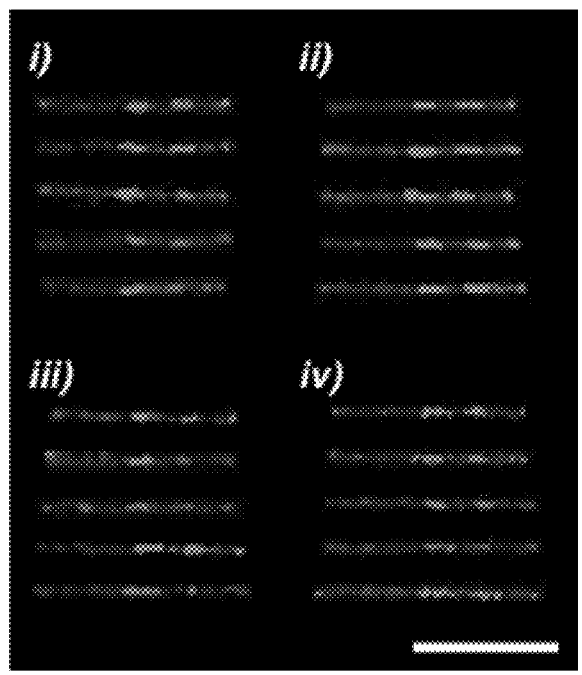

FIG. 3B shows λ DNA molecules stained with various combinations of fluorescent protein-DNA binding protein according to an embodiment of the present invention. The respective combinations are shown below (scale bar: 10 μm):

i) H-NS-mCherry and BRCA1-eGFP, ii) H-NS-mCherry and 2(KW)$_2$-eGFP, iii) 2HMG-mCherry and BRCA1-eGFP, and iv) 2HMG-mCherry and 2(KW)$_2$-eGFP.

Figure 3C:
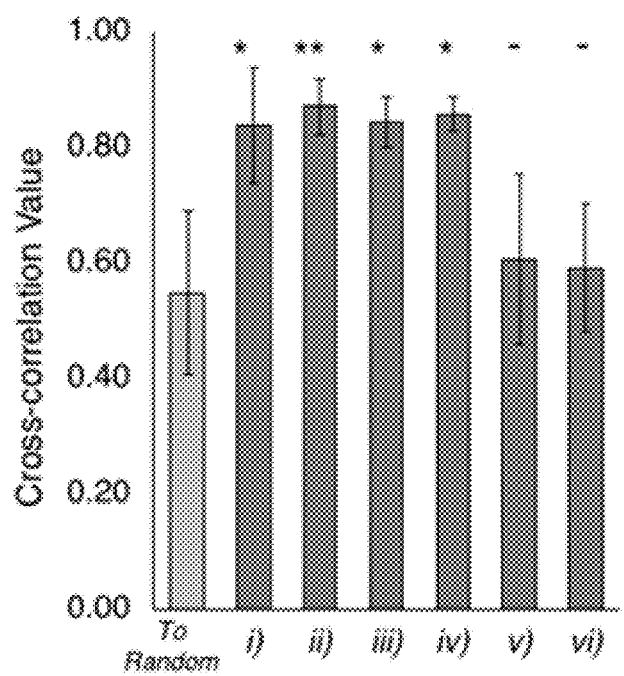

FIG. 3C is a graph showing cross-correlation values of λ DNA molecules stained with various combinations of fluorescent protein-DNA binding protein according to an embodiment of the present invention (Random: 0.55±0.14, i: 0.84±0.10, ii: 0.87±0.05, iii: 0.84±0.04, iv: 0.86±0.03, v: 0.61±0.15, and vi: 0.59±0.11) ($*p<0.02$, $**p<0.005$).

Figure 4:
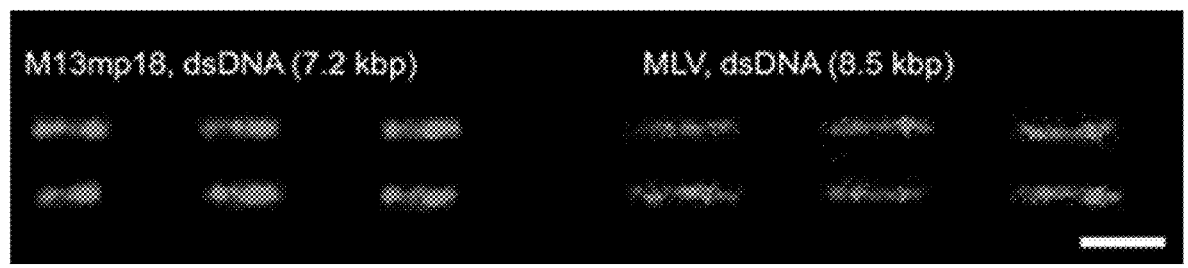

FIG. 4 schematically shows viral genomic DNA molecules stained with H-NS-mCherry and BRCA1-eGFP according to an embodiment of the present invention (scale bar: 5 μm).

DETAILED DESCRIPTION

Hereinafter, the present invention will be described in more detail with reference to examples. These examples are only for illustrating the present invention more specifically, and it will be apparent to those skilled in the art that the scope of the present invention is not limited by these examples.

Test Materials and Reagents

DNA primers were purchased from Cosmogenetech (Korea). Biotin-labeled DNA oligomers were purchased from Bioneer (Korea). *E. coli* BL21 (DE3) strain was purchased from Yeastern (Taiwan). λ DNA(NC_001416.1, 48,502 bp) and single-stranded M13mp18 (7,249 bp) were purchased from New England Biolabs (US). Epoxy was purchased from Devcon (US). N-trimethoxymethyl silyl propyl-N,N,N-trimethyl ammonium chloride (50% methanol) was purchased from Gelest (Morrisville, US). Ni-NTA agarose resin and column were purchased from Qiagen (Venlo, Netherlands). Unless note, all enzymes were purchased from NEB, and all reagents were purchased from Sigma-Aldrich.

Fluorescence Microscopy and DNA Visualization

An inverted optical microscope (Olympus IX70, Japan) was equipped with 60× and 100× Olympus UPlanSApo oil immersion objectives, and a LED light source (SOLA SM II light engine, Lumencor, US) was used. The light was condensed through corresponding filter sets (Semrock, US) to set excitation and emission wavelengths.

Fluorescence microscopic images were stored in a 16-bit TIFF format through an electron-multiplying charge-coupled device (EMCCD) digital camera device (Evolve EMCCD, Roper Scientific, US), and the software Micromanager was used. For image processing and analysis, the Java plug-in and python programs developed by the present inventors and ImageJ software were used.

Python Program imageCompare.py: a library of functions.

seq2map.py: converts a FASTA sequence file in silico map into an image with high frequency portions in white and low frequency portions in black.

insilicoMapFolder.py: scans and compares the in silico image file and the DNA image obtained from experiments for all images in a folder, and returns the position and value of a point with the highest cross-correlation coefficient, which are then stored in a new record file.

sortView.py: reads the record file obtained by insilicoMapFolder.py to visualize signal comparison, cross-correlation coefficient search, and image comparison and create the same in a new window.

randomtiff.py: creates tiff images having random brightness values.

Preparation of Fluorescent Protein-DNA Binding Protein

Plasmids necessary for protein production were constructed by overlap extension polymerase chain reaction (OE-PCR), which links a fluorescent protein to the C-terminal of DNA binding protein. The GGSGG linker containing glycine and serine was used, and respective primer sequences are shown in Table 1.

HNS-mCherry:

H-NS DNA was amplified using forward primer P1-HNS and reverse primer P2-HNS while DNA plug of *E. coli* MG1655 strain was used as template. mCherry DNA was amplified using the forward primer P3-mCherry and the reverse primer P4-mCherry. Then, H—NS and mCherry were linked with each other by overlap polymerase chain reaction.

BRCA1-eGFP:

BRCA1-DNA binding domain was amplified using the forward primer P5-BRCA and the reverse primer P6-BRCA while partial BRCA1 (Addgene plasmid #71116) including 452-1079 residues was used as a template. eGFP DNA was amplified using the forward primer P7-eGFP and the reverse primer P8-eGFP. Then, BRCA1 DNA binding domain and eGFP were linked with each other by overlap polymerase chain reaction.

2HMG-mCherry:

2HMG-mCherry was constructed by tagging DNA binding sites to each terminal of mCherry while the forward primer P9-HMG-mCherry and the reverse primer P10-HMG-mCherry were used.

2(KW)$_2$-mCherry:

2(KW)$_2$-mCherry was constructed by tagging DNA binding sites to each terminal of mCherry while the forward primer P11-(KW)$_2$-mCherry and the reverse primer P12-(KW)$_2$-mCherry were used.

2(KW)$_2$-eGFP:

2(KW)$_2$-eGFP was constructed by tagging DNA binding sites to each terminal of eGFP while the forward primer P13-(KW)$_2$-eGFP and the reverse primer P14-(KW)$_2$-eGFP were used.

2HMG-eGFP:

2HMG-eGFP was constructed by tagging DNA binding sites to each terminal of eGFP while the forward primer P15-HMG-eGFP and the reverse primer P16-HMG-eGFP were used.

TABLE 1

| SEQ ID NO | Name | Sequence (5'-3') |
|---|---|---|
| 1 | P1-HNS | ACTTCACATATGATGAGCGAAGCACTTAAAATTCTG |
| 2 | P2-HNS | GCCACCAGAACCACCTTGCTTGATCAGGAAATCGTCG |
| 3 | P3-mCherry | CAAGCAAGGTGGTTCTGGTGGCATGGTGAGCAAGGGCGAGGAG |
| 4 | P4-mCherry | ATTTCAGGATCCCTACTTGTACAGCTCGTCCATGCC |
| 5 | P5-BRCA | TATGCACATATGGTAGAGAGTAATATTGAAGACAAAATATTTGGG |
| 6 | P6-BRCA | GCTCACCATACCGCCGCTGCCACCTTTTGGCCCTCTGTTTCTACCTAG |
| 7 | P7-eGFP | GGTGGCAGCGGCGGTATGGTGAGCAAGGGCGAGGAG |
| 8 | P8-eGFP | TATGCAGGATCCTTACGCCTTGTACAGCTCGTCCATG |
| 9 | P9-HMG-mCherry | ATATTGCATATGACCCCGAAACGCCCGCGCGGCCGCCGAAAAAAGGCGGCAGCGGCGGC/ATGGTGAGCAAGGGCGAGGAG |

TABLE 1-continued

| SEQ ID NO | Name | Sequence (5'-3') |
|---|---|---|
| 10 | P10-HMG-mCherry | ATATTGGGATCCTTAGCCGCCGCTGCCGCCTTTTTC GGGCGGCCGCGCGGGCGTTTCGGGGT/CTTGTACAG CTCGTCCATGCC |
| 11 | P11-(KW)₂-mCherry | ATGTTGCATATGAAATGGAAATGGAAAAAAGCGATGGT GAGCAAGGGCGAGGAG |
| 12 | P12-(KW)₂-mCherry | ATGTTGGGATCCTTATTTCCATTTCCATTTTTTCGCCTT GTACAGCTCGTCCATGCC |
| 13 | P13-(KW)₂-eGFP | ATGTTGCATATGAAATGGAAATGGAAAAAAGCGATGC GTGAGCAAGGGCGAGGAGC |
| 14 | P14-(KW)₂-eGFP | ATGTTGGGATCCTTATTTCCATTTCCATTTTTTCGCCTT GTACAGCTCGTCCATGCC |
| 15 | P15-HMG-eGFP | ATATTGCATATGACCCCGAAACGCCCGCGCGGCCGCC CGAAAAAGGCGGCAGCGGCGGCATGCGTGAGCAAG GGCGAGGAGC |
| 16 | P16-HMG-eGFP | ATATTGGGATCCTTAGCCGCCGCTGCCGCCTTTTTC GGGCGGCCGCGCGGGCGTTTCGGGGTCTTGTACAGC TCGTCCATGCC |

Molecular Cloning

Using standard subcloning procedures, fluorescent protein-DNA binding protein sequences were inserted into the pET-15b vector and transformed into the *E. coli* BL21 (DE3) strains by using NdeI and BamHI. A single colony of the transformed cells was inoculated in fresh LB media containing ampicillin and incubated for 1 h.

After transformed cells were saturated, the cells were incubated to an optical density of about 0.8 at 37° C. with corresponding antibiotics. Fluorescent tagging proteins were overexpressed overnight with a final concentration of 1 mM for IPTG on a shaker at 20° C. and 250 rpm.

Cells for protein purification were harvested by centrifugation at 12,000×g, for 10 min (following centrifugations were all performed under similar conditions), and the residual media was washed with the cell lysis buffer (50 mM $Na_2HPO_4$, 300 mM NaCl, 10 mM Imidazole, pH 8.0). The cells were lysed by ultrasonication for 30 min and cell debris were centrifuged at 13,000 rpm for 10 min at 4° C. His-tagged FP-DNA binding proteins were purified using affinity chromatography with Ni-NTA agarose resin.

The mixture of cell protein and resin was kept on a shaking platform at 4° C. for 1 h. The lysate containing proteins bound Ni-NTA agarose resin was loaded onto the column for gravity chromatography and was washed several times using the protein washing buffer (50 mM $Na_2HPO_4$, 300 mM NaCl, 20 mM Imidazole, pH 8.0). Especially for H-NS-mCherry, a washing buffer containing 35 mM Imidazole (50 mM $Na_2HPO_4$, 300 mM NaCl, 35 mM Imidazole, pH 8.0) was used.

Finally, the bound proteins were eluted using a protein elution buffer (50 mM $Na_2HPO_4$, 300 mM NaCl, 250 mM imidazole, pH 8.0). All proteins were diluted (10 μg/mL) using 50% w/w glycerol/1×TE buffer (Tris 10 mM, EDTA 1 mM, pH 8.0).

Preparation of Coverslips and Modified Surfaces

Glass coverslips were inserted into the Teflon rack, and soaked in piranha etching solution (30:70 v/v $H_2O_2/H_2SO_4$) for 2 h, and then washed with deionized water until the pH reached the neutral (pH 7).

For positively-charged glass surfaces, 350 μL of N-trimethoxymethylsilylpropyl-N,N,N-trimethyl ammonium chloride dissolved in 50% methanol was mixed with 200 mL of deionized water.

To prepare glass surface for DNA tethering, 2 mL of N-[3-(trimethoxysilyl)propyl] ethylenediamine was added to 200 mL of methanol and 10 mL of glacial acetic acid to add primary amino groups. The glass coverslips were incubated in the solution for 30 min, sonicated for 15 min, and then incubated for 12 h at room temperature. Then, the coverslips were washed with methanol and ethanol.

Preparation of Microfluidic Devices

To investigate DNA elongation and deposition on positively charged surfaces, polydimethylsiloxane (PDMS) microfluidic devices were manufactured employing a standard rapid phototyping method.

More specifically, the patterns on a silicon wafer for microchannels (4 μm high and 100 μm wide) were fabricated using SU-8 2005 photoresist (Microchem, US). The PDMS pre-polymer mixed with a curing agent (10:1 weight ratio) was cast on the patterned wafer and cured at 65° C. for 4 h or longer. The cured PDMS was peeled off from the patterned wafer, and the PDMS devices were treated in an air plasma generator for 1 min with 100 W (Femto Science Cute Basic, Korea) to make PDMS surface hydrophilic. The PDMS devices were stored in water and air-dried before use.

Experimental Example 1: Confirmation of DNA Staining at Single-Molecule Level

A composition for DNA sequence analysis was prepared by mixing 50 μL of 8 nM H-NS-mCherry and 50 μL of 40 nM BRCA1-eGFP at a ratio of 1:1.

First, 10 μL of a solution obtained by diluting λ DNA to 15 ng/μL with 1×TE (10 mM Tris, 1 mM EDTA, pH 8) was mixed with 10 μL of the composition for DNA sequence analysis. After incubation at room temperature for a while, the mixture was diluted with 1×TE solution to 1/10-1/20, and then loaded at the entrance of a structure with a positively charged glass surface and a PDMS microchannel (100 μm×4 μm). Thereafter, DNA molecules were imaged on the microscope.

Figure 1A:
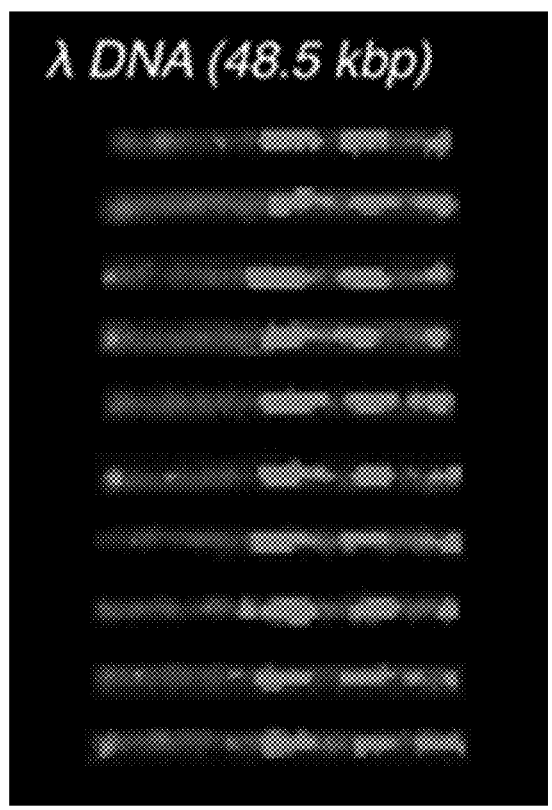
FIG. 1A schematically shows stained DNA molecules according to an embodiment of the present invention, and specifically, λ DNA molecules stained with H-NS-mCherry and BRCA1-eGFP.

As can be confirmed in FIG. 1A, as a result of staining of λ DNA using H-NS-mCherry and BRCA1-eGFP, λ DNA molecules could be aligned based on three distinct red spots on a green DNA backbone.

Next, 3 µL of a solution obtained by diluting λ DNA to 1/10-1/20 with the 1×TE solution was dropped on the positively charged glass surface, which was then brought in contact with a slide glass to spread the solution, and imaged by a fluorescence microscope.

Figures 1B, 2:
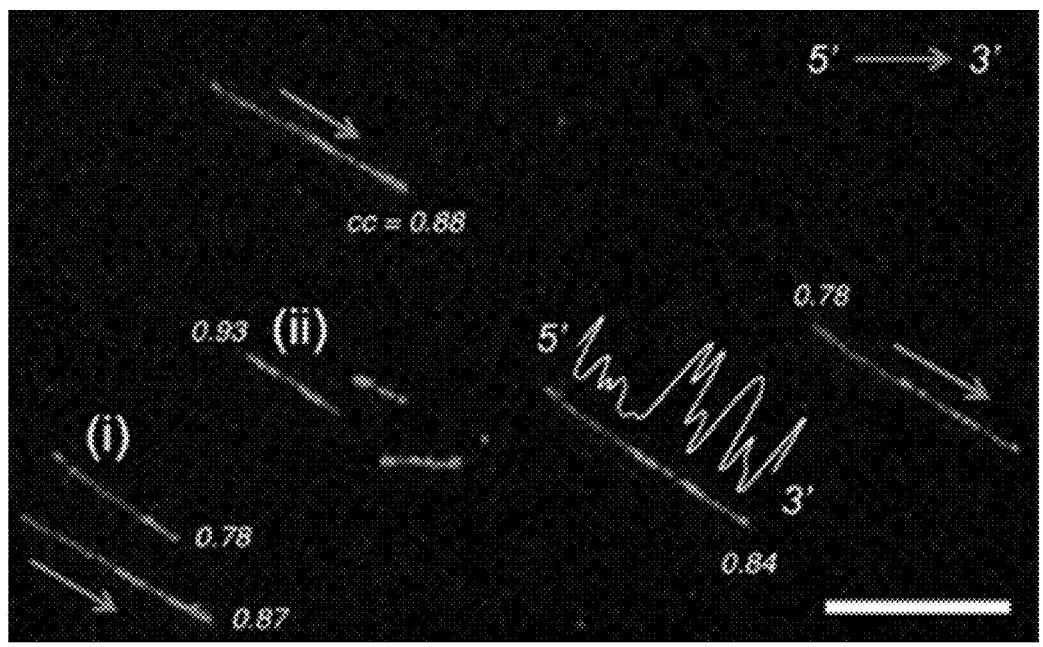
FIG. 1B shows stained DNA molecules according to an embodiment of the present invention. The arrows indicate molecular orientations of 5' to 3'; the white profile indicates the A/T frequency of λ DNA (scale bar: 10 μm), and respective numerical values indicate cross-correlation values (cc).
FIG. 2 shows λ DNA molecules stained with H-NS-mCherry and BRCA1-eGFP at various concentrations according to an embodiment of the present invention. Respective numerical values indicate cross-correlation values (cc).

As can be confirmed in FIG. 1B, λ DNA molecules were deposited on the positively charged surface. The alignment orientations of the randomly aligned DNA molecules can be obtained, and even in the case of the middle-broken DNA molecules but not the full molecule, the position information of corresponding fragments can be obtained.

Experimental Example 2: Confirmation of Optimal Concentration of Fluorescent Protein—DNA Binding Protein H-NS-mCherry at various concentrations (1, 2, 4, 8, or 16 nM) was mixed with BRCA1-eGFP (0, 10, or 20 nM) to prepare compositions for DNA sequence analysis, and λ DNA was visualized using PDMS microchannels by the method in Experimental Example 1".

As can be confirmed in FIG. 2, the stained DNA color pattern was varied according to the concentration of the fluorescent protein-DNA binding protein.

More specifically, the use of 1 nM H-NS-mCherry and 20 nM BRCA1-eGFP generated a full green DNA molecule, but in contrast, the use of 16 nM H-NS-mCherry and 10 nM BRCA1-eGFP generated a full red DNA molecule. The optimal concentration was shown at the ratio of 4 nM H-NS-mCherry and 20 nM BRCA1-eGFP (the cc value is 0.91: the cross-correlation coefficient (hereinafter, cc) was evaluated by using the following equation).

$$cc = \frac{\sum_{i=1}^{n}(x_i - \bar{x})(y_i - \bar{y})}{\sqrt{\sum_{i=1}^{n}(x_i - \bar{x})^2}\sqrt{\sum_{i=1}^{n}(y_i - \bar{y})^2}}$$

(n=number of samples; $x_i$, $y_i$=value at each point; and $\bar{x}$, $\bar{y}$=average of samples)

Meanwhile, the use of only H-NS-mCherry generated nucleotide sequence (A/T)-specific color patterns at 4 nM or lower. These results indicate that H-NS-mCherry stains NT-rich regions and BRCA1-eGFP complementarily stains the parts of DNA, which were not stained by H-NS-mCherry.

Experimental Example 3: Confirmation of Various Combinations of Fluorescent Protein-DNA Binding Protein On the basis of mCherry and eGFP fluorescent proteins, various combinations of fluorescent protein-DNA binding protein (H-NS-mCherry, BRCA1-eGFP, 2HMG-mCherry, 2(KW)$_2$-mCherry, 2(KW)$_2$-eGFP, 2HMG-eGFP) were used to produce compositions for DNA sequence analysis. λ DNA was visualized using positively charged glass surface by the method in Experimental Example 1.

As can be confirmed in FIGS. 3A and 3B, four (I, ii, iii, and iv) out of six combinations generated NT-specific λ genome patterns. On the contrary, random patterns (cc=0.61) were generated when both of the DNA binding proteins employ A/T-specific DNA binding proteins (H-NS and 2HMG) (v), and random patterns (cc=0.59) were also generated when both of the DNA binding proteins employ A/T-non-specific DNA binding proteins (BRCA1 and 2(KW)$_2$) (vi).

Experimental Example 4. Confirmation of DNA Staining at Short-DNA Fragment Level It was further investigated with reference to the above example results whether the composition of the present invention was applicable in short DNA fragments, such as M13, a bacteriophage that infects bacteria, and murine leukemia virus (MLV), a retrovirus that infects mice.

More specifically, as for the M13 phage genome, the double-stranded M13mp18 was synthesized from single-stranded circular DNA by Top polymerase reaction with a primer (GGAAACCGA GGAAACGCAATAATAACG-GAATACCC) (SEQ ID NO: 20). After the polymerase reaction, the double-stranded circular DNA was linearized by PstI. The double-stranded retroviral genomic DNA was synthesized from murine leukemia virus genome. After the reaction, the circular dsDNA was linearized by BmtI.

Each viral DNA was visualized, by the method in Experimental example 1, using the composition for DNA sequence analysis in which 50 µL of 8 nM H-NS-mCherry and 50 µL of 40 nM BRCA1-eGFP were mixed at a ratio of 1:1.

As can be confirmed in FIG. 4, the linearized DNA molecules were two-color stained to generate genome-specific patterns. It was confirmed that M13 DNA and MLV DNA could be differentiated from each other based on such image patterns.

CONCLUSION

From the integration of the description, it could be confirmed that, by using a combination of two complementary color fusion proteins, the composition of the present invention specifically stains DNA AT-rich regions, and shows an AT-rich sequence-specific fluorescence intensity pattern on the DNA backbone when binding to DNA. The use of such sequence-specific patterns, when the full sequences are provided, can determine DNA sequences from microscopic images of stained DNA, and therefore, the composition of the present invention can be helpfully used in the high-rate and high-efficiency analysis of giant single DNA molecules.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

This application contains references to amino acid sequences and/or nucleic acid sequences which have been submitted concurrently herewith as the sequence listing text file entitled "62406982_1.TXT", file size 11 KiloBytes (KB), created on 7 Jun. 2022. The aforementioned sequence listing is hereby incorporated by reference in its entirety pursuant to 37 C.F.R. § 1.52(e)(5).

What is claimed is:

1. A method for DNA sequence analysis, the method comprising treating a sample with a composition comprising:
    an adenine/thymine (A/T)-specific DNA binding protein linked with a first fluorescent protein;
    an NT-non-specific DNA binding protein linked with a second fluorescent protein;
    wherein the NT-specific DNA binding protein is a histone-like nucleoid-structuring (H-NS) protein or a high mobility group (HMG); and
    comparing the NT frequency of the entire genome of an analysis target and the A/T frequency of the sample treated with the composition;
    wherein the NT-non-specific DNA binding protein is a breast cancer 1 (BRCA1) protein or a protein having a structure of Chemical Formula 1 below:

$(XY)_n$,    [Chemical Formula 1]

wherein X and Y each are independently any amino acid independently selected from lysine (K), tryptophane (W), or derivatives thereof;
    wherein n is an integer of 1 to 5; and
    wherein the concentration ratio of the A/T-specific DNA binding protein linked with the first fluorescent protein and the A/T-non-specific DNA binding protein linked with the second fluorescent protein is 1:2-5.

2. The method of claim 1, wherein the sample is a single DNA molecule.

3. The method of claim 1, wherein the first fluorescent protein and the second fluorescent protein exhibit different colors.

4. The method of claim 3, wherein the first fluorescent protein is mCherry.

5. The method of claim 3, wherein the second fluorescent protein is enhanced green fluorescent protein (eGCP).

6. The method of claim 1, wherein the first fluorescent protein is mCherry.

7. The method of claim 1, wherein the second fluorescent protein is enhanced green fluorescent protein (eGCP).

* * * * *

SEQUENCE LISTING

<160> NUMBER OF SEQ ID NOS: 20

<210> SEQ ID NO 1
<211> LENGTH: 36
<212> TYPE: DNA
<213> ORGANISM: Artificial Sequence
<220> FEATURE:
<223> OTHER INFORMATION: P1-HNS

<400> SEQUENCE: 1
acttcacata tgatgagcga agcacttaaa attctg                    36

<210> SEQ ID NO 2
<211> LENGTH: 37
<212> TYPE: DNA
<213> ORGANISM: Artificial Sequence
<220> FEATURE:
<223> OTHER INFORMATION: P2-HNS

<400> SEQUENCE: 2
gccaccagaa ccaccttgct tgatcaggaa atcgtcg                   37

<210> SEQ ID NO 3
<211> LENGTH: 43
<212> TYPE: DNA
<213> ORGANISM: Artificial Sequence
<220> FEATURE:
<223> OTHER INFORMATION: P3-mCherry

<400> SEQUENCE: 3
caagcaaggt ggttctggtg gcatggtgag caagggcgag gag            43

<210> SEQ ID NO 4
<211> LENGTH: 36
<212> TYPE: DNA
<213> ORGANISM: Artificial Sequence
<220> FEATURE:
<223> OTHER INFORMATION: P4-mCherry

<400> SEQUENCE: 4
atttcaggat ccctacttgt acagctcgtc catgcc                    36

<210> SEQ ID NO 5
<211> LENGTH: 45
<212> TYPE: DNA
<213> ORGANISM: Artificial Sequence
<220> FEATURE:
<223> OTHER INFORMATION: P5-BRCA

<400> SEQUENCE: 5
tatgcacata tggtagagag taatattgaa gacaaaatat ttggg          45

<210> SEQ ID NO 6
<211> LENGTH: 48
<212> TYPE: DNA
<213> ORGANISM: Artificial Sequence
<220> FEATURE:
<223> OTHER INFORMATION: P6-BRCA

<400> SEQUENCE: 6
gctcaccata ccgccgctgc cacctttggg ccctctgttt ctacctag       48

<210> SEQ ID NO 7
<211> LENGTH: 36
<212> TYPE: DNA
<213> ORGANISM: Artificial Sequence

```
<220> FEATURE:
<223> OTHER INFORMATION: P7-eGFP

<400> SEQUENCE: 7
ggtggcagcg gcggtatggt gagcaagggc gaggag                          36

<210> SEQ ID NO 8
<211> LENGTH: 37
<212> TYPE: DNA
<213> ORGANISM: Artificial Sequence
<220> FEATURE:
<223> OTHER INFORMATION: P8-eGFP

<400> SEQUENCE: 8
tatgcaggat ccttacgcct tgtacagctc gtccatg                         37

<210> SEQ ID NO 9
<211> LENGTH: 81
<212> TYPE: DNA
<213> ORGANISM: Artificial Sequence
<220> FEATURE:
<223> OTHER INFORMATION: P9-HMG-mCherry

<400> SEQUENCE: 9
atattgcata tgaccccgaa acgcccgcgc ggccgcccga aaaaggcgg cagcggcggc    60 atggtgagca agggcgagga g                                           81

<210> SEQ ID NO 10
<211> LENGTH: 84
<212> TYPE: DNA
<213> ORGANISM: Artificial Sequence
<220> FEATURE:
<223> OTHER INFORMATION: P10-HMG-mCherry

<400> SEQUENCE: 10
atattgggat ccttagccgc cgctgccgcc ttttttcggg cggccgcgcg ggcgtttcgg    60
ggtcttgtac agctcgtcca tgcc                                        84

<210> SEQ ID NO 11
<211> LENGTH: 54
<212> TYPE: DNA
<213> ORGANISM: Artificial Sequence
<220> FEATURE:
<223> OTHER INFORMATION: P11-(KW)2-mCherry

<400> SEQUENCE: 11
atgttgcata tgaaatggaa atggaaaaaa gcgatggtga gcaagggcga ggag          54

<210> SEQ ID NO 12
<211> LENGTH: 57
<212> TYPE: DNA
<213> ORGANISM: Artificial Sequence
<220> FEATURE:
<223> OTHER INFORMATION: P12-(KW)2-mCherry

<400> SEQUENCE: 12
atgttgggat ccttatttcc atttccattt tttcgccttg tacagctcgt ccatgcc       57

<210> SEQ ID NO 13
<211> LENGTH: 56
<212> TYPE: DNA
<213> ORGANISM: Artificial Sequence
<220> FEATURE:
<223> OTHER INFORMATION: P13-(KW)2-eGFP
```

<400> SEQUENCE: 13
atgttgcata tgaaatggaa atggaaaaaa gcgatgcgtg agcaagggcg aggagc       56

<210> SEQ ID NO 14
<211> LENGTH: 57
<212> TYPE: DNA
<213> ORGANISM: Artificial Sequence
<220> FEATURE:
<223> OTHER INFORMATION: P14-(KW)2-eGFP

<400> SEQUENCE: 14
atgttgggat ccttatttcc atttccattt tttcgccttg tacagctcgt ccatgcc      57

<210> SEQ ID NO 15
<211> LENGTH: 83
<212> TYPE: DNA
<213> ORGANISM: Artificial Sequence
<220> FEATURE:
<223> OTHER INFORMATION: P15-HMG-eGFP

<400> SEQUENCE: 15
atattgcata tgaccccgaa acgcccgcgc ggccgcccga aaaaggcgg cagcggcggc    60 atgcgtgagc aagggcgagg agc                                          83

<210> SEQ ID NO 16
<211> LENGTH: 84
<212> TYPE: DNA
<213> ORGANISM: Artificial Sequence
<220> FEATURE:
<223> OTHER INFORMATION: P16-HMG-eGFP

<400> SEQUENCE: 16
atattgggat ccttagccgc cgctgccgcc ttttttcggg cggccgcgcg ggcgtttcgg   60
ggtcttgtac agctcgtcca tgcc                                         84

<210> SEQ ID NO 17
<211> LENGTH: 139
<212> TYPE: PRT
<213> ORGANISM: Unknown
<220> FEATURE:
<223> OTHER INFORMATION: histone-like nucleoid-structuring

<400> SEQUENCE: 17

His Met Met Ser Glu Ala Leu Lys Ile Leu Asn Asn Ile Arg Thr Leu
1               5                   10                  15

Arg Ala Gln Ala Arg Glu Cys Thr Leu Glu Thr Leu Glu Glu Met Leu
            20                  25                  30

Glu Lys Leu Glu Val Val Val Asn Glu Arg Arg Glu Glu Glu Ser Ala
        35                  40                  45

Ala Ala Ala Glu Val Glu Glu Arg Thr Arg Lys Leu Gln Gln Tyr Arg
    50                  55                  60

Glu Met Leu Ile Ala Asp Gly Ile Asp Pro Asn Glu Leu Leu Asn Ser
65                  70                  75                  80

Leu Ala Ala Val Lys Ser Gly Thr Lys Ala Lys Arg Ala Gln Arg Pro
                85                  90                  95

Ala Lys Tyr Ser Tyr Val Asp Glu Asn Gly Glu Thr Lys Thr Trp Thr
            100                 105                 110

Gly Gln Gly Arg Thr Pro Ala Val Ile Lys Lys Ala Met Asp Glu Gln
        115                 120                 125

Gly Lys Ser Leu Asp Asp Phe Leu Ile Lys Gln

```
            130                 135

<210> SEQ ID NO 18
<211> LENGTH: 11
<212> TYPE: PRT
<213> ORGANISM: Unknown
<220> FEATURE:
<223> OTHER INFORMATION: high mobility group

<400> SEQUENCE: 18

Thr Pro Lys Arg Pro Arg Gly Arg Pro Lys Lys
1               5                   10

<210> SEQ ID NO 19
<211> LENGTH: 628
<212> TYPE: PRT
<213> ORGANISM: Unknown
<220> FEATURE:
<223> OTHER INFORMATION: breast cancer 1

<400> SEQUENCE: 19

Val Glu Ser Asn Ile Glu Asp Lys Ile Phe Gly Lys Thr Tyr Arg Lys
1               5                   10                  15

Lys Ala Ser Leu Pro Asn Leu Ser His Val Thr Glu Asn Leu Ile Ile
            20                  25                  30

Gly Ala Phe Val Thr Glu Pro Gln Ile Ile Gln Glu Arg Pro Leu Thr
        35                  40                  45

Asn Lys Leu Lys Arg Lys Arg Arg Pro Thr Ser Gly Leu His Pro Glu
    50                  55                  60

Asp Phe Ile Lys Lys Ala Asp Leu Ala Val Gln Lys Thr Pro Glu Met
65                  70                  75                  80

Ile Asn Gln Gly Thr Asn Gln Thr Glu Gln Asn Gly Gln Val Met Asn
                85                  90                  95

Ile Thr Asn Ser Gly His Glu Asn Lys Thr Lys Gly Asp Ser Ile Gln
            100                 105                 110

Asn Glu Lys Asn Pro Asn Pro Ile Glu Ser Leu Glu Lys Glu Ser Ala
        115                 120                 125

Phe Lys Thr Lys Ala Glu Pro Ile Ser Ser Ser Ile Ser Asn Met Glu
    130                 135                 140

Leu Glu Leu Asn Ile His Asn Ser Lys Ala Pro Lys Lys Asn Arg Leu
145                 150                 155                 160

Arg Arg Lys Ser Ser Thr Arg His Ile His Ala Leu Glu Leu Val Val
                165                 170                 175

Ser Arg Asn Leu Ser Pro Pro Asn Cys Thr Glu Leu Gln Ile Asp Ser
            180                 185                 190

Cys Ser Ser Ser Glu Glu Ile Lys Lys Lys Tyr Asn Gln Met Pro
        195                 200                 205

Val Arg His Ser Arg Asn Leu Gln Leu Met Glu Gly Lys Glu Pro Ala
    210                 215                 220

Thr Gly Ala Lys Lys Ser Asn Lys Pro Asn Glu Gln Thr Ser Lys Arg
225                 230                 235                 240

His Asp Ser Asp Thr Phe Pro Glu Leu Lys Leu Thr Asn Ala Pro Gly
                245                 250                 255

Ser Phe Thr Lys Cys Ser Asn Thr Ser Glu Leu Lys Glu Phe Val Asn
            260                 265                 270

Pro Ser Leu Pro Arg Glu Glu Lys Glu Glu Lys Leu Glu Thr Val Lys
        275                 280                 285
```

-continued

Val Ser Asn Asn Ala Glu Asp Pro Lys Asp Leu Met Leu Ser Gly Glu
    290                 295                 300

Arg Val Leu Gln Thr Glu Arg Ser Val Glu Ser Ser Ile Ser Leu
305                 310                 315                 320

Val Pro Gly Thr Asp Tyr Gly Thr Gln Glu Ser Ile Ser Leu Leu Glu
                325                 330                 335

Val Ser Thr Leu Gly Lys Ala Lys Thr Glu Pro Asn Lys Cys Val Ser
                340                 345                 350

Gln Cys Ala Ala Phe Glu Asn Pro Lys Gly Leu Ile His Gly Cys Ser
                355                 360                 365

Lys Asp Asn Arg Asn Asp Thr Glu Gly Phe Lys Tyr Pro Leu Gly His
370                 375                 380

Glu Val Asn His Ser Arg Glu Thr Ser Ile Glu Met Glu Glu Ser Glu
385                 390                 395                 400

Leu Asp Ala Gln Tyr Leu Gln Asn Thr Phe Lys Val Ser Lys Arg Gln
                405                 410                 415

Ser Phe Ala Pro Phe Ser Asn Pro Gly Asn Ala Glu Glu Glu Cys Ala
                420                 425                 430

Thr Phe Ser Ala His Ser Gly Ser Leu Lys Lys Gln Ser Pro Lys Val
                435                 440                 445

Thr Phe Glu Cys Glu Gln Lys Glu Glu Asn Gln Gly Lys Asn Glu Ser
450                 455                 460

Asn Ile Lys Pro Val Gln Thr Val Asn Ile Thr Ala Gly Phe Pro Val
465                 470                 475                 480

Val Gly Gln Lys Asp Lys Pro Val Asp Asn Ala Lys Cys Ser Ile Lys
                485                 490                 495

Gly Gly Ser Arg Phe Cys Leu Ser Ser Gln Phe Arg Gly Asn Glu Thr
                500                 505                 510

Gly Leu Ile Thr Pro Asn Lys His Gly Leu Leu Gln Asn Pro Tyr Arg
                515                 520                 525

Ile Pro Pro Leu Phe Pro Ile Lys Ser Phe Val Lys Thr Lys Cys Lys
530                 535                 540

Lys Asn Leu Leu Glu Glu Asn Phe Glu Glu His Ser Met Ser Pro Glu
545                 550                 555                 560

Arg Glu Met Gly Asn Glu Asn Ile Pro Ser Thr Val Ser Thr Ile Ser
                565                 570                 575

Arg Asn Asn Ile Arg Glu Asn Val Phe Lys Glu Ala Ser Ser Ser Asn
                580                 585                 590

Ile Asn Glu Val Gly Ser Ser Thr Asn Glu Val Gly Ser Ser Ile Asn
                595                 600                 605

Glu Ile Gly Ser Ser Asp Glu Asn Ile Gln Ala Glu Leu Gly Arg Asn
610                 615                 620

Arg Gly Pro Lys
625

<210> SEQ ID NO 20
<211> LENGTH: 35
<212> TYPE: DNA
<213> ORGANISM: Artificial Sequence
<220> FEATURE:
<223> OTHER INFORMATION: primer

<400> SEQUENCE: 20
ggaaaccgag gaaacgcaat aataacggaa taccc                    35